(12) United States Patent
Eriksson

(10) Patent No.: US 6,572,883 B1
(45) Date of Patent: Jun. 3, 2003

(54) ILLNESS CURATIVE COMPRISING FERMENTED FISH

(75) Inventor: Jan Eriksson, Österfärnebo (SE)

(73) Assignee: Realisec AB, Österfärnebo (SE)

(*) Notice: Subject to any disclaimer, the term of this patent is extended or adjusted under 35 U.S.C. 154(b) by 0 days.

(21) Appl. No.: 09/522,720

(22) Filed: Mar. 10, 2000

(30) Foreign Application Priority Data

Mar. 10, 1999 (SE) .............................................. 9900846
Oct. 20, 1999 (SE) .............................................. 9903771

(51) Int. Cl.⁷ .......................... A61K 9/48; A61K 47/00; A61K 9/20; A23K 1/17; A23B 4/12
(52) U.S. Cl. ....................... 424/451; 424/439; 424/442; 424/451; 424/464; 426/7; 426/385; 426/574; 426/643
(58) Field of Search .................. 424/439, 442, 424/464, 489; 426/7, 385, 574, 643

(56) References Cited

U.S. PATENT DOCUMENTS 3,773,523 A * 11/1973 Chhuy et al. ................ 426/167
3,903,267 A * 9/1975 Miler et al. .................. 424/195

FOREIGN PATENT DOCUMENTS

| JP | 07227245 A | * 8/1995 |
| WO | 97-00621 | 1/1997 |
| WO | 97/24933 | 7/1997 |

OTHER PUBLICATIONS

English translate abstract of JP07227245A.*

* cited by examiner

*Primary Examiner*—Thurman K. Page
*Assistant Examiner*—S. Tran
(74) *Attorney, Agent, or Firm*—Dilworth & Barrese, LLP

(57) ABSTRACT

An agent for curing states of illness in the digestive apparatus comprising fish fermented by a fermentation process in brine. According to a first method for the production of the agent the fermented fish is encased in capsules that are essentially impermeable to the scent agents that are emitted by the fermented fish. According to a second method for the production of the agent fermented fish in a finely divided form is formed into units, for instance tablets or cookies, and is brought into an essentially solid form. The invention also comprises use of a preparation comprising fermented fish for curing states of illness in the digestive apparatus. Likewise, the invention comprises a method for curing states of illness in the digestive apparatus, wherein a preparation comprising fermented fish is administered to a patient/an animal. Furthermore, the invention comprises an animal feeding stuff comprising fermented fish and methods for the production of such an animal feeding stuff.

19 Claims, No Drawings

ILLNESS CURATIVE COMPRISING FERMENTED FISH

FIELD OF THE INVENTION AND PRIOR ART

The invention relates to an agent and a method for curing states of illness in the digestive apparatus. The invention also comprises a method for the production of such an agent and use of a preparation as such an agent. Furthermore, the invention relates to an animal feeding stuff and a method for the production of an animal feeding stuff. The invention also relates to a method for the production of a preparation for use in an agent for curing states of illness in the digestive apparatus and a product intended for use in an animal feeding stuff.

For treatment of illnesses occurring in the stomach, which cause indisposition, vomiting and diarrhoeas and which in more severe cases may result in catarrhs or inflammations in the bowels, for instance enterocolitis, a number of different agent are used. Activated carbon may be mentioned as an example of such agents. The activated carbon absorbs exotoxins from pathogenic micro-organisms but has no effect on the micro-organisms that are causing the state of illness. Nor does the carbon have any favourable influence on the re-establishment of the normal bacterial flora. Another example is antibiotics, such as penicillin and streptomycin. Such can certainly be used but they possess the disadvantage that they can cause injuries on the stomach and intestinal tract. Other medicaments, such as for instance the medicament offered for sale by AB Astra under the trademark "LOSEC", control the acid production in the digestive apparatus and can therefor have a negative effect on the organism, in particular when being used during a longer period of time. These medicaments also possess the disadvantage that they are very costly.

It is per se known that certain lactic acid fermented food stuffs can have a favourable effect on the digestion and that lactic acid bacteria may prevent the establishment of pathogenic bacteria in the intestine.

A state of illness in the stomach which is frequent in the modern society is caused by negative stress, which may manifest itself in serious disturbances in the digestive apparatus.

Stomach illnesses of the kind mentioned above are frequent also among domestic animals. In order to handle these stomach illnesses a number of different preparations and methods have been applied. Some methods are based on a reduction of the fibre and fat content in the food intake, in order thereby to alleviate diarrhoeas. However, with these methods the underlying problem is not attacked. What is achieved is a limitation of the nutrients that an illness effected stomach and intestine system not fully can assimilate, whereby the visible signs of diarrhoea are reduced. However, with these methods no influence on the micro-organisms that cause the state of illness is achieved. Nor do these methods have any favourable influence on the re-establishment of the normal bacterial flora. Other methods are based on the use of antibiotica. However, the use of antibiotica in animal feeding stuff results in different types of undesired side-effects among the animals. Furthermore, a frequent use of antibiotica involves the risk for the development of antibiotics resistant bacteria. In Sweden the use of antibiotica in animal feeding stuff has been limited by legislation.

It is per se known to use an additive of lactic acid bacteria in animal feeding stuff as an alternative to antibiotica, which additive is considered to have a favourable effect on the intestine flora.

SUMMARY OF THE INVENTION

The object of the present invention is to provide an agent suitable for curing states of illness in the digestive apparatus, which agent on one hand is effective, on the other hand won't have any negative effect on humans or animals. Furthermore, the object of the invention is to provide methods, by means of which the agent in question can be manufactured in a rational and comparatively inexpensive way.

According to the invention this object is achieved by means of the features of a fish fermented by a fermentation process in brine, or a preparation comprising fish fermented by a fermentation process in brine being encased in capsules made of edible material, which capsules are essentially impermeable to the scent agents that are emitted by the fermented fish, or a fish fermented by a fermentation process in brine in a finely divided form being formed into units, for instant tablets or cookies, and being brought into an essentially solid form.

A further object of the present invention is to provide an animal feeding stuff, which besides supplying nutrients has a favourable effect on the digestive apparatus of animals, without causing any negative effect on the animals. Furthermore, the object of the invention is to provide methods, by means of which the animal feeding stuff in question can be manufactured in a rational and comparatively inexpensive way.

According to the invention this object is achieved by means of the features the units having an outer layer of edible material or a fish fermented by a fermentation process in brine preferably in finely divided form and being formed into units, e.g. pellets, and being brought into an essentially solid form.

Consequently, the present invention is based on the understanding that fish, for instance Baltic herring, fermented by a fermentation process in brine has a very favourable effect on the digestive apparatus, and is able to cure or alleviate the states of illness previously referred to.

A kind of fish that for a long time back has been treated by fermentation in brine is Baltic herring. The fish product thus obtained is called "surströmming" (fermented Baltic herring). The choice of Baltic herring as primary product for the fermentation process described hereinafter has only been done for the purpose of exemplification. However, the invention is in no way limited to fermented Baltic herring, on the contrary it comprises the use of all the fishes that by their constitution are suitable for treatment by a fermentation process in brine. Other examples of such fishes are smelt, roach and shark.

During fermentation of fermented Baltic herring lactic acid bacteria is the active micro-flora. The lactic acid bacteria produce organic acids, lactic acid at first hand, which reduce the pH-value of the Baltic herring. Such organic acids cause an inhibition of the activity of pathogenic bacteria. A low pH tends to act selectively bacteriostatic, since bacteria of families such as Lactobacillus and Escherichia, which are good for the organism, are favoured by a low pH, whereas pathogenic bacteria, such as Salmonella and Vibrio, are inhibited, as already indicated.

Fermented Baltic herring can also have other favourable effects on the organism. In connection with tests performed with the agent according to the invention, a surprisingly good effect on a wide spectrum of states of illness in the stomach, especially disturbances of the stomach function caused by stress, has been observed.

In connection with tests performed with the animal feeding stuff according to the invention, a surprisingly good effect on states of illness in the stomach of animals, such as horses and dogs, has been observed.

Fermented Baltic herring is a food stuff that has been known for long. However, its extraordinary favourable effect on states of illness in the digestive apparatus has not been described in the literature. For the production of fermented Baltic herring it is of vital importance that the salting is performed to a correct degree and that the fermentation is made to take place in a controlled way. In this connection, the temperature conditions are essential. A theory behind the present invention is that the specific methodology, comprising a light salting and fermentation, used for the production of fermented Baltic herring results in a combination of substances and a bacterial flora that are particularly favourable for the digestive apparatus. The constitution of the Baltic herring, which in itself is favourable for the digestive apparatus, is here also supposed to contribute to the favourable effect. It is emphasised that the used primary product, the Baltic herring, must not be to fat. A too fat Baltic herring will cause rancidity, since it will be possible for other bacteria, which are unfavourable to the digestive apparatus, to grow. Spawning Baltic herring will give the best result as it has a lean flesh.

Fermented Baltic herring was previously consumed to a larger extent, since it had the advantage that the preservation could be achieved with a small amount of salt, which was very expensive at that time. Today, fermented Baltic herring is produced on a small scale, since other possibilities for long-term storage of foodstuff are available. Nowadays, fermented Baltic herring has an almost "exotic" character. Its very unpleasant smell has a strongly restraining effect on a more widespread use thereof. Normally, fermented Baltic herring is probably consumed rather seldom even by confirmed lovers of fermented Baltic herring. In particular in densely built-up communities, the unpleasant smell is probably the most restraining factor. This is probably the reason why the good effects on the digestive apparatus of the fermented Baltic herring has not previously been observed. Contributing to this is also that the states of illness, for which the fermented Baltic herring is particularly effective, for instance stomach disorders caused by stress, is a rather modern phenomenon.

The agent or animal feeding stuff according to the invention can also comprise a certain amount of the brine from the fermentation process that the fermented fish has been subjected to. Because active micro-flora is present also in the brine. This brine can also be present in the form of an extract obtained for instance by evaporation of the brine. By the evaporation the water included in the brine is vaporised, whereby a concentrated solution of the substances included in the brine is obtained.

In order, according to the invention, to create opportunities for use of the favourable effects of the fish fermented by a fermentation process in brine on states of illness in the stomach, an embodiment of the invention is based on the idea of encasing the fermented fish in capsules made of edible material, which capsules are essentially impermeable to the scent agents that are emitted by the fermented fish and that give for instance the fermented Baltic herring its characteristic smell. Such an encapsulation of for instance the fermented Baltic herring implies that opportunities are created for consuming the fermented Baltic herring in such a way that the surroundings won't be exposed to said smell. The material of the capsules is chosen so that it will be dissolved by the stomach contents, i.e. only after the capsules have reached the stomach. However, the material of the capsules must not be so difficult to dissolve that they will be transported too far in the digestive apparatus by the peristalsis before the fermented fish is set free. As an example, it may be mentioned that gelatine capsules have turned out to be favourable. However, any kind of suitable capsule material, which sets the fermented fish free only after the capsules have reached into the stomach, can be used.

Capsules formed in this way have turned out to effectively prevent that not even persons intimately near to the person who has consumed the capsules can perceive that the person in question has consumed fermented Baltic herring, which in its free form has such a strong smell, or other fish fermented in brine. Expressed in other words, this implies that the consumption of the fermented fish with the aid of such capsules can be done without the surroundings being bothered by the smell of the fermented fish in any way. Consequently, opportunities are thereby created for a person effected by states of illness in the digestive apparatus to regularly consume capsules during the period when the person is awake, i.e. during work as well as time off. The agent according to the invention, with fermented fish encased in capsules, implies a supply of both nutrition and constituents active against the state of illness in connection with the consumption thereof.

A separate capsule can contain 2–10 gramme fermented fish in order to give a suitable size for easy swallowing, but the dose of fermented fish in a separate capsule can be larger as well as smaller than that.

It is preferred that the fish preparation in a capsule consists of finely divided fermented fish. This creates opportunities for a rational industrial encapsulation of the preparation. However, within the scope of the invention is also comprised that the fermented fish is divided into pieces and that one or several such pieces are inserted into a separate capsule.

The capsule can also comprise not only the flesh from the fermented fish but also a certain amount of brine from the fermentation process that the fermented fish has been subjected to, or an extract thereof. Consequently, this implies that the preparation comprising fermented fish, if the fermented fish is in a finely divided form, will be pumpable so that it rationally can be inserted into the capsules. This can also be achieved by adding to the finely divided fermented fish another brine or liquid than the brine that emanates from the fermentation process.

The invention also comprises an animal feeding stuff comprising fish fermented by a fermentation process in brine, which in the way described above is encased in capsules made of edible material, which capsules are essentially impermeable to the scent agents that are emitted by the fermented fish. In this way, it will be easier to make animals, which are sensitive for instance to the characteristic smell of the fermented Baltic herring, accept an animal feeding stuff comprising fermented Baltic herring.

According to an embodiment of the invention, the agent comprising fermented fish is present in units of essentially solid form, for instance formed as tablets or cookies, said units comprising fermented fish in a finely divided form and possibly a binding agent of edible material, for instance gelatine. In this way, the agent can be provided in a form that allows a rational production, handling and administration.

The invention also comprises an animal feeding stuff provided in units of essentially solid form, for instance formed as pellets, said units comprising fermented fish in a finely divided form and possibly a binding agent of edible material, for instance gelatine.

By providing said units with an outer layer of edible material, for instance gelatine or other suitable material, the units can be given desired characteristics. Said layer can for instance be of a material that makes the layer essentially impermeable to the scent agents that are emitted by the fermented fish, whereby advantages are obtained corresponding to those discussed above in connection with the embodiment with capsules. The layer can also have flavourings that give the units desired taste characteristics. The material of the layer can also be chosen so that the units will get a smooth surface and thereby will be easy to swallow. Furthermore, the layer can have such a composition that it, by its chemical structure or by acting obstructing against the penetration of bacteria, acts preservative on the fermented fish comprised in the units. By means of said layer other characteristics of the units, such as colour, structure etc., can also be adapted after desire and need. The layer can also be formed so that several of the characteristics mentioned above are obtained simultaneously.

According to preferred embodiments of the invention, the agent and the animal feeding stuff comprise freeze-dried fermented fish. By means of freeze-drying a product of fermented fish is obtained, which easily and rationally can be handled industrially. The freeze-dried fermented fish can for instance be finely divided into a powder, for instance by grinding in connection with or after the freeze-drying process, for subsequent treatment such as encapsulation or tablet pressing. In connection with tests it has been found that the freeze-drying won't cause any reduction of the constituents of the fermented fish that are active and favourable to the digestive system. However, by the freeze-drying an advantageous reduction of the substances that give the fermented Baltic herring its characteristic smell is obtained.

The invention also comprises a method for the production of a preparation for use in agents for curing states of illness in the digestive apparatus and a method for the production of a product intended for use in an animal feeding stuff, the preparation/product being produced by fish fermented by a fermentation process in brine and subjected to freeze-drying. In order to expedite the freeze-drying process, the fermented fish can be divided into small pieces or finely divided before the freeze-drying. During the freeze-drying, the fermented fish can also be present together with a certain amount of brine from the fermentation process that the fermented fish has been subjected to or together with an extract thereof obtained by, for instance, evaporation.

Freeze-drying, or sublimation drying, as the process is also called, implies drying of a product in a frozen state. The ice is then directly transformed into vapour without passing the liquid state, i.e. it sublimes. For this to take place, the evaporation must take place below the triple point (0.0098° C., 610.8 Pa), at which all three phases (solid, liquid, vapour) can exist simultaneously. A freeze-drying unit normally consists of a freezing equipment, a drying chamber, and a condenser with a vacuum pump. The product is normally frozen in a special equipment and thereafter placed on, for instance, trays in a drying chamber. Thereafter, the drying chamber is rapidly evacuated and heat is supplied either via heating plates, on which the trays are placed, or through radiant heat. The formed vapour is condensed into ice on the tubes of the condenser, the temperature of which is 15–20° C. lower than the sublimation temperature. The process can take place batchwise or in a continuous unit.

The invention also comprises use of the preparation comprising fermented fish fermented by a fermentation process in brine as an agent for curing states of illness in the digested apparatus, or a preparation encased in capsules made of edible materials, which capsules are essentially impermeable to the scent agents that are emitted by the fermented fish or a preparation containing finely divided fermented fish which is present in units of essentially solid form, for instance formed as tablets or cookies, or a preparation comprising freeze-dried fermented fish, or a preparation comprising fermented Baltic herring; and, a process for curing states of illness in the digestive apparatus comprising a preparation having fish fermented by a fermentation process in brine being administered to a patient/animal, or preparation being administered in freeze-dried form, or preparation being encased in capsules of edible material, or preparation being administered in the form of units of essentially solid form, for instance formed as tablets or cookies, these units comprising finely divided fermented fish or a preparation comprising fermented Baltic herring.

For the production of fermented Baltic herring one can proceed such that the Baltic herring is first put into a brine in ungutted condition for extraction of blood from the fish. Thereafter, the fish is gutted by removal of the head and the entrails, the roe and the milt however being retained. An alternative is to first gut the Baltic herring and thereafter put it in brine for leaching the blood from the fish.

The fish, thus gutted, but however with the roe and milt still remaining, is thereafter put into a new brine in smaller barrels, which are closed by means of lids. The brine here used has a salt content being in the interval 11–14 percentage by weight. The barrels are filled with brine and Baltic herring so that a small space of air is left at the top of the barrels. This is, based on experience, essential for the development of the fermentation process. The microorganisms serving for the fermentation are naturally contained in the Baltic herring. After about two months the fermentation process has given the desired result and the fermented Baltic herring is then prepared. During the fermentation process the temperature should not be too high, since this could destroy the fermented Baltic herring.

The fermented Baltic herring that is to be encapsulated is thereafter prepared by forming into pieces, pulverization or grinding and a liquid may then possibly be added according to what has previously been described, whereupon the obtained preparation is inserted into the capsules. The preparing may also be done by freeze-drying of whole, divided or finely divided fermented Baltic herring, possibly with a subsequent pulverization.

Fermented Baltic herring which is to be formed into units of an essentially solid form is prepared by pulverization or grinding, possibly after preceding freeze-drying, whereupon binding agent is possibly added. By means of suitable equipment, for instance a tablet pressing machine or equipment for the production of pellets, the mixture is then formed into units of desired shape and is brought into an essentially solid form. In accordance with what has previously been described, the units can be provided with an outer layer of suitable material. The application of this layer can, depending on what is suitable for the separate production process, take place before or after the units have been brought into their intended shape, or simultaneously therewith.

It is hereby pointed out that the present invention does not exclude that the fermented fish comprised in the agent/ animal feeding stuff is admixed with an additive adapted to promote the ability to cure states of illness or an additive favourable for instance to the process of encapsulation or pressing of tablets. Examples of such additives are consistency controllers. The animal feeding stuff according to the invention can of course comprise a larger or smaller amount of fermented fish. The animal feeding stuff can for instance completely or for a major part consist of fermented fish, possibly supplemented with the addition of substances being suitable from a nutritional point of view or suitable in any other way. However, the fermented fish comprised in the animal feeding stuff can also constitute a smaller ingredient in the animal feeding stuff and can for instance constitute an additive to one or several ingredients constituting the main ingredients of the animal feeding stuff.

A non-limiting example of the production of the agent according to the invention will follow below.

EXAMPLE 1

Newly caught lean Baltic herring is gutted by removal of the head and entrails. The roe and milt are remained. The gutted Baltic herring is put into a brine and is stirred so as to get properly mixed with the brine. The brine extracts the blood out of the fish. Thereafter the blood containing brine is poured away.

75 kg gutted Baltic herring is put into a barrel with a volume of 110 litres. Brine with a salt content of 11–14 percentage by weight is added to the barrel. The brine is filled in the barrel so that a space of air remains at the top. Thereafter a lid is applied to the barrel. During the next few days the barrel is rolled a couple of times for achievement of a proper mixing. Thereafter the barrel is left and the fermentation process will work by itself. After up to two months a high-quality fermented Baltic herring has been obtained.

The fermented Baltic herring is grinded into a mass and by means of a conventional or arbitrary encapsulation equipment the mass of fermented Baltic herring is applied into capsules of gelatine in a way known per se. These are made to fully encase the mass of fermented Baltic herring and are to be capable of durably containing the mass within the capsules. The capsules are further chosen so that they won't allow escape of substances from the fermented Baltic herring that makes it possible to determine, on the outside of the capsules, the contents of the capsules by the sense of smell.

The obtained capsules contain a product that is high-grade from a nutritional point of view and has an excellent ability to counteract states of illness in the digestive apparatus The agent according to the invention can be administered to humans as well as animals. It is completely harmless to consume; it can be consumed by the patient up to a feeling of satisfaction.

It is realised that an animal feeding stuff according to the invention can also be produced according to the example described above.

EXAMPLE 2

Newly caught lean Baltic herring is treated in the way described in connection with Example 1 for preparation of fermented Baltic herring.

The fermented Baltic herring is thereafter divided into small pieces and is freeze-dried by means of a conventional or arbitrary freeze-drying equipment. The fermented Baltic herring may here be part of a mixture, which also comprises a certain amount of the brine from the fermentation process the fermented Baltic herring has been subjected to or an extract thereof, for instance obtained by evaporation. After the freeze-drying the fermented Baltic herring is grinded into a meal-like powder. A binding agent, for instance gelatine, is added to the powder, whereupon the thereby obtained mixture is compressed into tablets in a conventional or arbitrary tablet pressing machine.

The obtained tablets can then, in any suitable way, be provided with an outer layer of the kind previously mentioned.

An animal feeding stuff according to the invention can also be produced according to a method corresponding to the method described in the example above, in which case the mixture consisting of fermented Baltic herring grinded into a powder, possibly after the addition of a binding agent, is suitably formed into pellets by means of a conventional or arbitrary equipment for the production of feed-pellets.

It is again worth emphasising that the choice of just Baltic herring as the primary product in the examples above only has been made for the purpose of exemplification. The invention is however, as previously pointed out, in no way limited to fermented Baltic herring, on the contrary it embraces the use of all the fishes that by their constitution are suitable for treatment by a fermentation process in brine.

It is further emphasised that the invention is not only limited to the exemplifying specifications given above. Consequently, variations of details may take place within the scope of the inventional idea in the way this idea emerges in the subsequent claims.

What is claimed is:

1. A composition for curing states of illness in the digestive system,
   comprising an effective amount of fish fermented by a fermentation process in brine, for treating the digestive illness,
   the fermented fish, together, where appropriate, with the brine or the extract thereof, is encased in capsules made of edible material, which capsules are essentially impermeable to the unpleasant smell emitted by the fermented fish, and
   lactic acid bacteria as active micro-flora, serving to generate lactic acid, reducing pH value of the fish and inhibiting activity of pathogenic bacteria in the digestive system with said low pH tending to act selectively bacteriostatic, such that bacteria of families Lactobacillus and Escherichia being favored by said low pH and pathogenic bacteria Salmonella and Vibrio being inhibited by said low pH.

2. A composition according to claim 1, wherein the composition comprises finely divided fermented fish.

3. A composition according to claim 1, wherein the composition comprises freeze-dried fermented fish.

4. A composition according to claim 1, wherein the composite composition further comprises brine from the fermentation process the fish has been subjected to, or an extract thereof.

5. A composition according to claim 1, comprises fermented Baltic herring.

6. A composition according to claim 1, containing 2–10 grams of fermented fish in each said capsule.

7. A composition according to claim 1, additionally comprising brine from said fermentation process.

8. A composition according to claim 1, comprising particles of fermented Baltic herring in brine being encapsulated in gelatin.

9. A method for curing states of illness in the digestive system, comprising the steps of
   encasing a preparation comprising fish fermented by a fermentation process in brine together, where appropriate, with the brine or extract thereof, in capsules made of edible material, which capsules are essentially impermeable to the unpleasant smell emitted by the fermented fish, the fermented fish comprising lactic acid bacteria as active micro-flora, serving to generate lactic acid, reducing pH value of the fish and inhibiting activity of pathogenic bacteria in the digestive system with said low pH tending to act selectively bacteriostatic, such that bacteria of families Lactobacillus and Escherichia being favored by said low pH and pathogenic bacteria Salmonella and Vibrio being inhibited by said low pH, and administering to a human or animal suffering from illness in the digestive tract, an effective amount of said preparation for treating said illness.

10. A method according to claim 9, wherein the preparation is prepared by pulverization of fermented fish.

11. A method according to claim 9, characterized in that the preparation is prepared of fermented Baltic herring.

12. A method according to claim 9, which is wherein the fermented fish subjected to freeze-drying.

13. A method according to claim 12, wherein the fermented fish is divided into small pieces or is finely divided before it is freeze-dried.

14. A method according to claim 12, wherein the fermented fish is freeze-dried together with a certain amount of the brine from the fermentation process the fish has been subjected to or together with an extract thereof, for instance obtained by evaporation.

15. A method according to claim 12, wherein the fermented fish is finely divided during the freeze-drying or after it has been freeze-dried.

16. A method according to claim 12, wherein the fermented fish is fermented Baltic herring.

17. The method according to claim 9, wherein the preparation contains finely divided fermented fish, which is present in units of essentially solid form.

18. A method according to claim 9, wherein the preparation comprises freeze-dried fermented fish.

19. A method according to claim 9, wherein the preparation comprises fermented Baltic herring.

* * * * *